(12) United States Patent
Clawson et al.

(10) Patent No.: US 8,971,501 B2
(45) Date of Patent: Mar. 3, 2015

(54) METHODS AND SYSTEMS TO IDENTIFY CODE HIERARCHY BIAS IN MEDICAL PRIORITY DISPATCH SYSTEMS

(75) Inventors: Jeffrey J. Clawson, Salt Lake City, UT (US); Richard M. Saalsaa, Salt Lake City, UT (US)

(73) Assignee: Priority Dispatch Corporation, Salt Lake City, UT (US)

( * ) Notice: Subject to any disclaimer, the term of this patent is extended or adjusted under 35 U.S.C. 154(b) by 1076 days.

(21) Appl. No.: 12/422,561

(22) Filed: Apr. 13, 2009

(65) Prior Publication Data

US 2010/0260325 A1    Oct. 14, 2010

(51) Int. Cl.
*H04M 11/04* (2006.01)
*G06F 19/00* (2011.01)
*G06Q 50/22* (2012.01)

(52) U.S. Cl.
CPC .............. *G06F 19/327* (2013.01); *G06Q 50/22* (2013.01); *G06F 19/363* (2013.01)
USPC .............................................. 379/45; 379/38

(58) Field of Classification Search
CPC .............. H04M 3/5116; H04M 11/04; H04M 2203/357; H04M 2242/04; H04M 2242/14; H04M 3/42; H04M 3/42357; H04M 3/5183; H04M 7/0024; H04M 1/72536; H04M 1/72538; G06F 19/3431; G06F 19/363; G06F 19/345; G06F 19/327; G06F 19/3418
USPC ............ 379/37, 38, 45, 49, 265.01; 455/404, 455/404.2, 457, 404.1, 521, 415; 705/1.1, 705/2, 3, 325; 340/539.12, 539.13; 607/5, 607/60; 700/108
See application file for complete search history.

(56) References Cited

U.S. PATENT DOCUMENTS

| | | | |
|---|---|---|---|
| 3,799,147 | A | 3/1974 | Adolph et al. |
| 4,130,881 | A | 12/1978 | Haessler et al. |
| 4,164,320 | A | 8/1979 | Irazoqui et al. |
| 4,237,344 | A | 12/1980 | Moore |
| 4,290,114 | A | 9/1981 | Sinay |
| 4,338,493 | A | 7/1982 | Stenhuis et al. |

(Continued)

FOREIGN PATENT DOCUMENTS

| | | |
|---|---|---|
| CN | 101169840 A | 4/2008 |
| CN | 201117055 Y | 9/2008 |

(Continued)

OTHER PUBLICATIONS

Office Action for U.S. Appl. No. 12/268,963, filed Nov. 11, 2008, mailed from USPTO on Jul. 29, 2011, 18 pgs.

(Continued)

*Primary Examiner* — Akelaw Teshale
(74) *Attorney, Agent, or Firm* — John R. Thompson; Stoel Rives LLP

(57) ABSTRACT

A system and method assists an emergency medical dispatcher in responding to emergency calls by generating a determinant level code. A computer implemented method to determine Code Hierarchy Bias generates a determinant level sub-code that can be stored and analyzed with the determinant level code to determine the nature of Code Hierarchy Bias, to reveal hidden signs, symptoms, and conditions, to improve the accuracy and usefulness of determinant level codes, and to tailor emergency medical response structure for a more efficient use of emergency response personnel and resources.

22 Claims, 12 Drawing Sheets

(56) References Cited

U.S. PATENT DOCUMENTS

| | | |
|---|---|---|
| 4,360,345 A | 11/1982 | Hon |
| 4,455,548 A | 6/1984 | Burnett |
| 4,489,387 A | 12/1984 | Lamb et al. |
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |
| 5,072,383 A | 12/1991 | Brimm et al. |
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |
| 5,193,855 A | 3/1993 | Shamos |
| 5,228,449 A | 7/1993 | Christ et al. |
| 5,253,164 A | 10/1993 | Holloway et al. |
| 5,255,187 A | 10/1993 | Sorensen |
| 5,291,399 A | 3/1994 | Chaco |
| 5,323,444 A | 6/1994 | Ertz et al. |
| 5,339,351 A | 8/1994 | Hoskinson et al. |
| 5,348,008 A | 9/1994 | Bornn et al. |
| 5,379,337 A | 1/1995 | Castillo et al. |
| 5,404,292 A | 4/1995 | Hendrickson |
| 5,410,471 A | 4/1995 | Alyfuku et al. |
| 5,423,061 A | 6/1995 | Fumarolo et al. |
| 5,438,996 A | 8/1995 | Kemper et al. |
| 5,441,047 A | 8/1995 | David et al. |
| 5,462,051 A | 10/1995 | Oka et al. |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,536,084 A | 7/1996 | Curtis et al. |
| 5,544,649 A | 8/1996 | David et al. |
| 5,554,031 A | 9/1996 | Moir et al. |
| 5,590,269 A | 12/1996 | Kruse et al. |
| 5,594,638 A | 1/1997 | Iliff |
| 5,594,786 A | 1/1997 | Chaco et al. |
| 5,596,994 A | 1/1997 | Bro |
| 5,630,125 A | 5/1997 | Zellweger |
| 5,636,873 A | 6/1997 | Sonsteby |
| 5,650,995 A | 7/1997 | Kent |
| 5,660,176 A | 8/1997 | Iliff |
| 5,675,372 A | 10/1997 | Aguayo, Jr. et al. |
| 5,682,419 A | 10/1997 | Grube et al. |
| 5,684,860 A | 11/1997 | Milani et al. |
| 5,689,229 A | 11/1997 | Chaco et al. |
| 5,719,918 A | 2/1998 | Serbetciouglu et al. |
| 5,722,418 A | 3/1998 | Bro |
| 5,724,983 A | 3/1998 | Selker et al. |
| 5,734,706 A | 3/1998 | Windsor et al. |
| 5,745,532 A | 4/1998 | Campana, Jr. |
| 5,748,907 A | 5/1998 | Crane |
| 5,754,960 A | 5/1998 | Downs et al. |
| 5,759,044 A | 6/1998 | Redmond |
| 5,761,278 A | 6/1998 | Pickett et al. |
| 5,761,493 A | 6/1998 | Blakeley et al. |
| 5,787,429 A | 7/1998 | Nikolin, Jr. |
| 5,805,670 A | 9/1998 | Pons et al. |
| 5,809,493 A | 9/1998 | Ahamed et al. |
| 5,822,544 A | 10/1998 | Chaco et al. |
| 5,823,948 A | 10/1998 | Ross, Jr. et al. |
| 5,826,077 A | 10/1998 | Blakeley et al. |
| 5,832,187 A | 11/1998 | Pedersen et al. |
| 5,842,173 A | 11/1998 | Strum et al. |
| 5,844,817 A | 12/1998 | Lobley et al. |
| 5,850,611 A | 12/1998 | Krebs |
| 5,857,966 A | 1/1999 | Clawson |
| 5,901,214 A | 5/1999 | Shaffer et al. |
| 5,902,234 A | 5/1999 | Webb |
| 5,910,987 A | 6/1999 | Ginter et al. |
| 5,912,818 A | 6/1999 | McGrady et al. |
| 5,915,019 A | 6/1999 | Ginter et al. |
| 5,926,526 A | 7/1999 | Rapaport et al. |
| 5,933,780 A | 8/1999 | Connor et al. |
| 5,961,446 A | 10/1999 | Beller et al. |
| 5,962,891 A | 10/1999 | Arai |
| 5,964,700 A | 10/1999 | Tallman et al. |
| 5,986,543 A | 11/1999 | Johnson |
| 5,989,187 A | 11/1999 | Clawson |
| 5,991,730 A | 11/1999 | Lubin et al. |
| 5,991,751 A | 11/1999 | Rivette et al. |
| 6,004,266 A * | 12/1999 | Clawson ............... 600/300 |
| 6,010,451 A | 1/2000 | Clawson |
| 6,022,315 A | 2/2000 | Iliff |
| 6,035,187 A | 3/2000 | Franza |
| 6,040,770 A | 3/2000 | Britton |
| 6,052,574 A | 4/2000 | Smith, Jr. |
| 6,053,864 A * | 4/2000 | Clawson ............... 600/300 |
| 6,058,179 A | 5/2000 | Shaffer et al. |
| 6,074,345 A | 6/2000 | van Oostrom et al. |
| 6,076,065 A | 6/2000 | Clawson |
| 6,078,894 A * | 6/2000 | Clawson et al. ........ 705/7.42 |
| 6,106,459 A | 8/2000 | Clawson |
| 6,112,083 A | 8/2000 | Sweet et al. |
| 6,115,646 A | 9/2000 | Fiszman et al. |
| 6,117,073 A | 9/2000 | Jones et al. |
| 6,118,866 A | 9/2000 | Shtivelman |
| 6,127,975 A | 10/2000 | Maloney |
| 6,134,105 A | 10/2000 | Lueker |
| 6,292,542 B1 | 9/2001 | Bilder |
| 6,370,234 B1 | 4/2002 | Kroll |
| 6,535,121 B2 | 3/2003 | Matheny |
| 6,594,634 B1 | 7/2003 | Hampton et al. |
| 6,607,481 B1 | 8/2003 | Clawson |
| 6,610,012 B2 | 8/2003 | Mault |
| 6,696,956 B1 | 2/2004 | Uchida et al. |
| 6,879,819 B2 | 4/2005 | Brooks |
| 6,901,397 B1 | 5/2005 | Moldenhauer et al. |
| 6,931,112 B1 | 8/2005 | McFarland et al. |
| 6,968,375 B1 | 11/2005 | Brown |
| 7,106,835 B2 | 9/2006 | Saalsaa |
| 7,194,395 B2 | 3/2007 | Genovese |
| 7,289,944 B1 | 10/2007 | Genovese |
| 7,428,301 B1 | 9/2008 | Clawson |
| 7,436,937 B2 | 10/2008 | Clawson |
| 7,645,234 B2 | 1/2010 | Clawson |
| 7,703,020 B2 | 4/2010 | Bhattaru |
| 7,783,586 B2 | 8/2010 | Friedlander et al. |
| 7,978,826 B2 | 7/2011 | Salafia et al. |
| 8,066,638 B2 | 11/2011 | Clawson |
| 8,103,523 B2 | 1/2012 | Clawson |
| 8,417,533 B2 | 4/2013 | Clawson |
| 8,494,868 B2 | 7/2013 | Saalsaa |
| 2002/0004729 A1 | 1/2002 | Zak et al. |
| 2002/0106059 A1 | 8/2002 | Kroll et al. |
| 2003/0028536 A1 | 2/2003 | Singh et al. |
| 2003/0050538 A1 | 3/2003 | Naghavi et al. |
| 2003/0187615 A1 | 10/2003 | Epler et al. |
| 2003/0195394 A1* | 10/2003 | Saalsaa ............... 600/300 |
| 2003/0212575 A1 | 11/2003 | Saalsaa et al. |
| 2005/0015115 A1 | 1/2005 | Sullivan et al. |
| 2006/0059423 A1 | 3/2006 | Lehmann et al. |
| 2006/0122520 A1 | 6/2006 | Banet et al. |
| 2006/0167346 A1 | 7/2006 | Sarel |
| 2006/0173500 A1 | 8/2006 | Walker et al. |
| 2006/0178908 A1 | 8/2006 | Rappaport |
| 2006/0212315 A1 | 9/2006 | Wiggins |
| 2006/0225213 A1 | 10/2006 | Tomcany |
| 2007/0055559 A1 | 3/2007 | Clawson |
| 2007/0112275 A1 | 5/2007 | Cooke et al. |
| 2007/0116189 A1 | 5/2007 | Clawson |
| 2007/0189480 A1 | 8/2007 | Salafia et al. |
| 2007/0201664 A1 | 8/2007 | Salafia et al. |
| 2008/0310600 A1 | 12/2008 | Clawson |
| 2009/0037374 A1 | 2/2009 | Delia et al. |
| 2009/0168975 A1 | 7/2009 | Clawson |
| 2009/0191529 A1 | 7/2009 | Mozingo et al. |

(56) References Cited

U.S. PATENT DOCUMENTS

| | | | |
|---|---|---|---|
| 2010/0004710 A1 | 1/2010 | Kellum | |
| 2010/0121156 A1 | 5/2010 | Yoo | |
| 2010/0152800 A1 | 6/2010 | Walker et al. | |
| 2010/0198755 A1 | 8/2010 | Soll et al. | |
| 2010/0257250 A1 | 10/2010 | Salafia et al. | |

FOREIGN PATENT DOCUMENTS

| | | |
|---|---|---|
| GB | 2471960 | 1/2011 |
| JP | 2002-049693 | 2/2002 |
| JP | 2003109162 A | 4/2003 |
| JP | 2003-187003 A | 7/2003 |
| JP | 2003256963 A | 9/2003 |
| JP | 2010033201 A | 12/2010 |
| KR | 10-2005-0085778 A | 8/2005 |
| KR | 10-2006-0084866 A | 7/2006 |
| KR | 20070043337 A | 4/2007 |
| KR | 10-2008-0004125 A | 1/2008 |
| KR | 10-2009-0014837 A | 2/2009 |
| WO | WO 2004030259 | 4/2004 |
| WO | WO2006/015229 A2 | 2/2006 |
| WO | WO 2008/014398 A2 | 1/2008 |
| WO | WO2008/156876 A1 | 12/2008 |
| WO | WO 2011031383 | 3/2011 |

OTHER PUBLICATIONS

International Search Report and Written Opinion mailed Jan. 19, 2011 in PCT Application No. PCT/US2010/043308, filed Jul. 27, 2010.
International Search Report and Written Opinion mailed Jan. 19, 2011 in PCT Application No. PCT/US2010/043311, filed Jul. 27, 2010.
Radosevich, Lynda, "Network holds sway on life, death," Computerworld, v27 n21, May 24, 1993, 2 pgs.
Harris, Roger, "Updated 911 Phone System Top Concern of Residents," Business First-Louisville, v9 n19 s1, Dec. 1992, 3 pgs.
"Geac Completes Software Install," Wireless Week, Nov. 18, 1996, 3 pgs.
"Dictaphone introduces Windows-based Computer-Aided Dispatch (CAD) system," Business Wire, Apr. 23, 1996, 2 pgs. (in commercial use in 1995).
Holroyd, Brian, et al., "Medical Control; Quality Assurance in Prehospital Care," JAMA, the Journal of American Medical Association, v256, n8, Aug. 1986, p. 1027-1031.
CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 mailed Dec. 31, 2003, 8 pgs.
Office Action Summary from USPTO for U.S. Appl. No. 10/255,901 mailed Oct. 13, 2004, 8 pgs.
Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
United States Patent Office, Office Action for U.S. Appl. No. 12/558,808, mailed Apr. 23, 2011.
Notification of Transmittal of the ISR (2 pgs.), ISR, (2 pgs.), and Written Opinion (8 pgs.) for PCT/US2009/040909 filed on Apr. 17, 2009; mailed from ISA on Jun. 10, 2009.
International Search Report and Written Opinion PCT/US2010/050402, filed on Sep. 27, 2010, and mailed from ISA on Apr. 27, 2011, 9 pgs.
International Search Report and Written Opinion for PCT/US2011/042543 filed on Jun. 30, 2011, and mailed from ISA on Feb. 9, 2012, 11 pgs.
International Search Report and Written Opinion for PCT/US2011/042582 filed on Jun. 30, 2011, and mailed from ISA on Feb. 9, 2012, 8 pgs.
International Preliminary Report of Patentability for PCT/US2010/043308 filed on Jul. 27, 2010 mailed Mar. 22, 2012, 6 pgs.
International Preliminary Report of Patentability for PCT/US2010/043311 filed on Jul. 27, 2010 mailed Mar. 29, 2012, 6 pgs.
Office Action Summary from USPTO for U.S. Appl. No. 12/5858,045 mailed Mar. 22, 2012, 9 pgs.
International Search Report and Written Opinion for PCT/US09/48577, International filed Jun. 25, 2009, mailed from ISA Aug. 7, 2009, 9 pgs.

(56) References Cited

OTHER PUBLICATIONS

International Preliminary Report on Patentability for PCT/US2009/048577 filed Jun. 25, 2009, mailed from WIPO on Oct. 27, 2011, 7 pgs.

Office Action for U.S. Appl. No. 12/396,201, filed Mar. 2, 2009 and mailed from USPTO on Mar. 8, 2011, 23 pgs.

International Search Report and Written Opinion for PCT/US2012/021867 filed Jan. 19, 2012, and mailed Aug. 30, 2012, 9 pgs.

Office Action Summary from USPTO for U.S. Appl. No. 13/605,501 mailed Nov. 18, 2013.

International Search Report and Written Opinion for PCT/US2013/055537 filed on Aug. 19, 2013 and mailed from ISA on Nov. 22, 2013.

Notice of Allowance from USPTO for U.S. Appl. No. 13/026,043 mailed Jan. 13, 2014.

Nor, A. Mohd, et al., "Agreement Between Ambulance Paramedic- and Physician-Recorded Neurological Signs With Face Arm Speech Test (FAST) in Acute Stroke Patients", http://stroke.ahajournals.org/content/35/6/1355, Apr. 29, 2004, visited Nov. 17, 2013, 3 pgs.

Liferidge, Aisha T., et al., "Ability of Laypersons to Use the Cincinnati Prehospital Stroke Scale", Prehospital Emergency Care, Elsevier, vol. 8, No. 4, Oct. 1, 2004, pp. 384-387.

Nordberg, Marie, "Dispatch Disasters," Emergency Medicine, Aug. 1995.

Notice of Allowance from USPTO for U.S. Appl. No. 10/255,901 mailed Feb. 20, 2013.

\* cited by examiner

METHODS AND SYSTEMS TO IDENTIFY CODE HIERARCHY BIAS IN MEDICAL PRIORITY DISPATCH SYSTEMS

TECHNICAL FIELD

This invention relates to computer systems and methods that provide medical protocol interrogation and instructions for emergency dispatch. More specifically, the invention is directed to systems and computer implemented methods to improve such emergency medical dispatch systems and methods.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Figure 1:
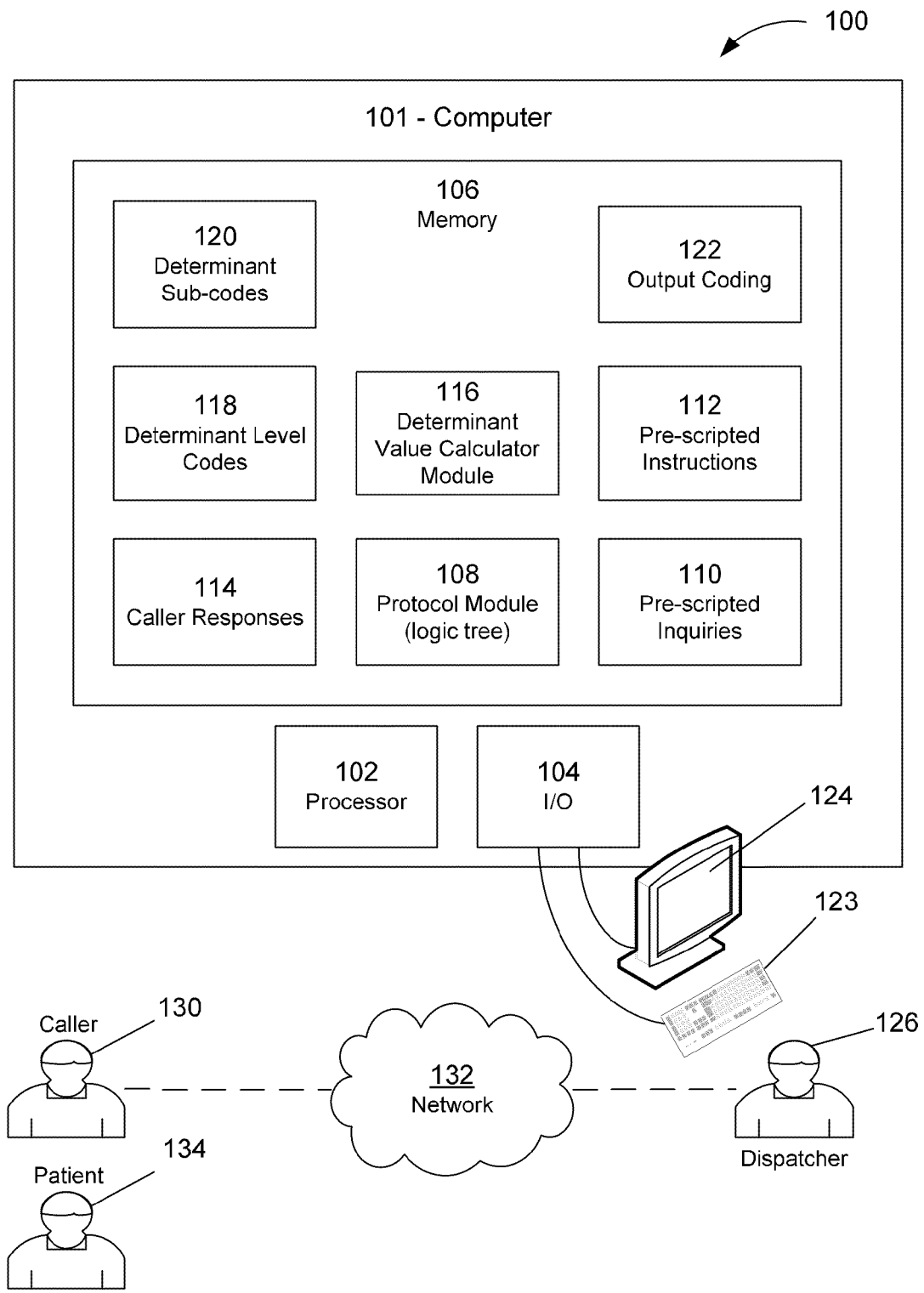
FIG. 1 depicts a block diagram of one embodiment of a system to identify code hierarchy bias in a medical priority dispatch system.

Thousands of calls requesting emergency medical services are made every year. Many of these calls are not true medical emergencies and some medical emergencies have higher priority than others, so it is important to prioritize the calls in several ways. For example, true emergency calls with the highest priority should be dispatched first. Moreover, if a response agency has units with different capabilities, the more severe medical problems should receive the more advanced units. Finally, if lights-and-siren are not needed from a medical standpoint, they should not be used, thereby increasing the safety of all those on the road and in the emergency vehicles.

An automated medical priority dispatch system ("MPDS") may aid a call taker, or emergency medical dispatcher ("EMD"), in prioritizing the calls. The MPDS may follow a protocol comprising a logic tree that provides the EMD with pre-scripted inquiries or questions to be directed to a caller, that presents potential responses from the caller, and that provides the EMD with instructions for the caller based on the responses of the caller. The pre-scripted inquiries may ask or prompt the caller to report aspects of the emergency situation being reported. Aspects of the emergency situation may include but are not limited to signs, symptoms, and conditions. The aspects may relate to the patient, the circumstances at the time of the incident, and the circumstances present as the call is proceeding. As can be appreciated, symptoms may relate primarily to a patient, whereas signs and conditions may relate to a patient or to circumstances surrounding the incident.

The caller responses may route to subsequent pre-scripted inquiries and/or instructions to the caller. The caller responses may be processed by the MPDS according to predetermined logic to generate a consistent and predictable dispatch response. In this manner, the MPDS also aids the EMD to provide both the correct emergency medical dispatch response and the appropriate doctor-approved post-dispatch instructions to the caller before professional help arrives. Exemplary embodiments of such medical dispatch systems and protocols are disclosed in U.S. Pat. Nos. 5,857,966, 5,989,187, 6,004,266, 6,010,451, 6,053,864, 6,076,065, 6,078,894, 6,106,459, 6,607,481, 7,106,835, and 7,428,301, which are incorporated herein by reference.

The MPDS can aid the EMD in categorizing and prioritizing emergency calls by generating a determinant level code that categorizes the type and level of the incident. The determinant level code may include an emergency type descriptor for the type of incident or situation, an emergency level descriptor indicating priority, and a determinant value. For example, a determinant level code "6-D-1" comprises an emergency type descriptor '6,' an emergency level descriptor 'D', and a determinant value '1.' The emergency type 6 indicates breathing problems. The emergency level D indicates that the response level is Delta. Some examples of possible emergency levels are C (for lowest level emergencies requiring a response level of Charlie), D (for mid-level emergencies requiring a response level of Delta), and E (for highest level emergencies requiring a response level of Echo). An emergency level descriptor and determinant value may be referred to together as a determinant. The MPDS may include a determinant calculator to calculate a determinant from the caller's responses to protocol questions. The determinant calculator may calculate the determinant by assigning a value to each aspect of a situation that may be reported in a caller response according to the clinical criticality of the aspect. In another embodiment, a calculator may simply calculate the determinant value. In still another embodiment, a calculator may calculate the determinant level code by calculating the determinant and then combining the determinant with the emergency type descriptor.

The determinant level code enables the EMD to dispatch an appropriate emergency response agency, such as police, fire department, paramedics, etc., to the scene of the emergency. The determinant level code also may be communicated to the response agency to aid in anticipating the type of response and resources needed for the particular emergency at the scene. Because the questions asked and the recommendations made may deal directly with life and death decisions, it is important for the protocol and/or the EMD to determine the correct determinant level code.

A commonly recurring challenge to generating a correct determinant level code for a situation arises when a caller or patient reports more than one aspect of a given situation, each of which may be similarly critical. When multiple aspects are reported that are similarly critical, the EMD and/or the MPDS may then be forced to make a choice that can affect how the protocol of the MPDS proceeds. Although aspects may be similarly critical, the aspects may be ranked hierarchically according to their clinical importance. The clinical importance may be derived from how critical or life threatening the aspect is from a clinical standpoint. Accordingly, a choice to focus on one aspect of the situation likely may result in generation of a determinant level code that is different than would be generated by another choice.

When the caller reports multiple similarly critical aspects, the MPDS may be programmed to pick a choice, or prompt the EMD to make a choice, based on the aspect with the highest ranking criticality. Even if the MPDS were not programmed to pick or prompt for a choice, the EMD may make his or her own subjective comparison of the reported aspects and choose based on perceived criticality. The choice recommended by the MPDS and/or made by the EMD introduces what may be referred to as Code Hierarchy Bias. Code Hierarchy Bias can be described as the tendency of MPDS logic, or an EMD, to make a particular choice when presented with a set of similarly critical aspects of an emergency situation. The emergency dispatch system industry does not currently realize this bias exists, and presently there are no means for determining the nature of the bias or how the bias may affect emergency dispatch.

Understanding how Code Hierarchy Bias affects emergency dispatch requires understanding the nature of the bias. Stated differently, it requires understanding why MPDS logic and/or a human EMD may select a particular determinant level code when multiple similarly critical aspects, such as signs, symptoms, or conditions, are concurrently present. Unfortunately, understanding the 'why' is not easy because the choices made are not presently trackable. Multiple reported aspects can result in cloaking of one or more of the reported signs, symptoms, or conditions, no matter the specific choice made.

The nature of emergency dispatch simply does not lend itself to capturing every reported aspect. As an example, the MPDS protocol may be designed to identify the most critical situations, inherently keying on the most critical aspects reported. Keying on the critical aspects can lead to filtering and generalizing a situation rather than distinguishing and detailing the situation. In other words, a determinant level code may merely approximate or partially describe a clinical presentation in a given emergency situation. Furthermore, an EMD may be primarily focused on rapid processing of the call, more intent on achieving a rapid response than an providing an accurate response. These characteristics, inherent to emergency dispatch, result in failure to gather data that can be used to determine whether the MPDS protocol facilitates correct emergency responses and how the MPDS and underlying protocol can be improved.

The present disclosure attempts to address these challenges by providing methods and systems for capturing and revealing the multiple reported aspects of emergency situations that may be cloaked or hidden by present emergency call processing, and thereby reveal the nature of Code Hierarchy Bias. An automated computer-implemented method according to the present disclosure, operating in association with an MPDS, can facilitate revealing Code Hierarchy Bias. Revealing Code Hierarchy Bias can enhance the ability, through scientific studies, to unlock hidden or overlooked conditions, to improve the accuracy and usefulness of determinant level code descriptors, and to tailor the Emergency Medical System response structure.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a computer-readable storage medium having stored thereon instructions that may be used to program a computer (or other electronic device) to perform processes described herein. The computer-readable storage medium may comprise a memory device, including but not limited to, hard drives, floppy diskettes, optical disks, USB drives, CD-ROMs, DVD-ROMs, ROMs, RAMs, EPROMs, EEPROMs, magnetic or optical cards, solid-state memory devices, or other types of media/machine-readable medium suitable for storing electronic instructions. For example, instructions for performing described processes may be transferred from a remote computer (e.g., a server) to a requesting computer (e.g., a client) by way of data signals via a communication link (e.g., network connection).

Several aspects of the embodiments described will be illustrated as software modules or components. As used herein, a software module or component may include any type of computer instruction or computer-executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

FIG. 1 depicts a block diagram of one embodiment of a computer system 100 to identify code hierarchy bias in an emergency medical dispatch system. The computer system 100 may comprise a computer 101 having a processor 102 coupled to input/output (I/O) and memory 106. The memory 106 may comprise a computer-readable storage medium. The memory 106 may include components of a medical priority dispatch system ("MPDS"), including a protocol module 108 to aid an emergency medical dispatcher (EMD) 126 in processing an emergency call, pre-scripted inquiries 110 and pre-scripted instructions 112 that the protocol module 108 can present to the EMD 126 by way of the computer monitor 124 or other display, and a determinant value calculator module 116 that determines an appropriate determinant value and/or determinant level code based on the caller responses 114 to the pre-scripted inquiries 110. The determinant value calculator module 116 of the memory 106 may further comprise a determinant level sub-code calculator to calculate a determinant level sub-code that can be used to identify Code Hierarchy Bias, as will be described in greater detail. The memory 106 may further include storage for caller responses 114 to the pre-scripted inquiries 110. The memory 106 may store pre-established determinant level codes 118 and determinant level sub-codes 120 from which the appropriate output coding 122 can be derived and stored. The determinant level codes 118 and the determinant level sub-codes may be stored as pairs, or otherwise associated together.

An emergency caller 130 can dial 9-1-1 to reach the local Emergency Medical System to seek assistance for an emergency situation involving a patient 134. The caller 130 can be connected to an EMD 126 over a voice communication network 132. The protocol module 108 is initiated to aid the EMD 126 in processing the call. The protocol module 108 can be initiated automatically by the MPDS as part of the call being received by the EMD 126. In another embodiment, the EMD 126 can initiate the protocol module 108, for example, by clicking a button on a graphical user interface displayed on the monitor 124. The protocol module 108 presents the EMD 126 with pre-scripted inquiries 110 and/or pre-scripted instructions 112 to be directed by the EMD 126 to the caller 130. The EMD 126 may read the pre-scripted questions 110 and/or instructions 112 to the caller 130 over the voice communication network 132.

The EMD 126 receives responses to the questions from the caller 130. The questions guide the caller 130 to gather information about the patient 134. As the caller responds to the questions, the information about the patient 134 is relayed by the caller 130 to the EMD 126 over the communication network 132. The EMD 126 inputs the caller responses into the MPDS using the keyboard 123 and/or a user interface displayed on the monitor 124. The caller responses 114 are stored in the memory 106. The processor 102 can process the caller responses to provide information that the protocol module 108 can use to determine how to proceed. The processor 102 can also process the responses to determine one or more candidate determinant level codes 118 and one or more determinant level sub-codes 120 that capture all the aspects of the situation reported by the caller 130 in the caller's responses 114 to the pre-scripted inquiries 110.

Figure 1A:
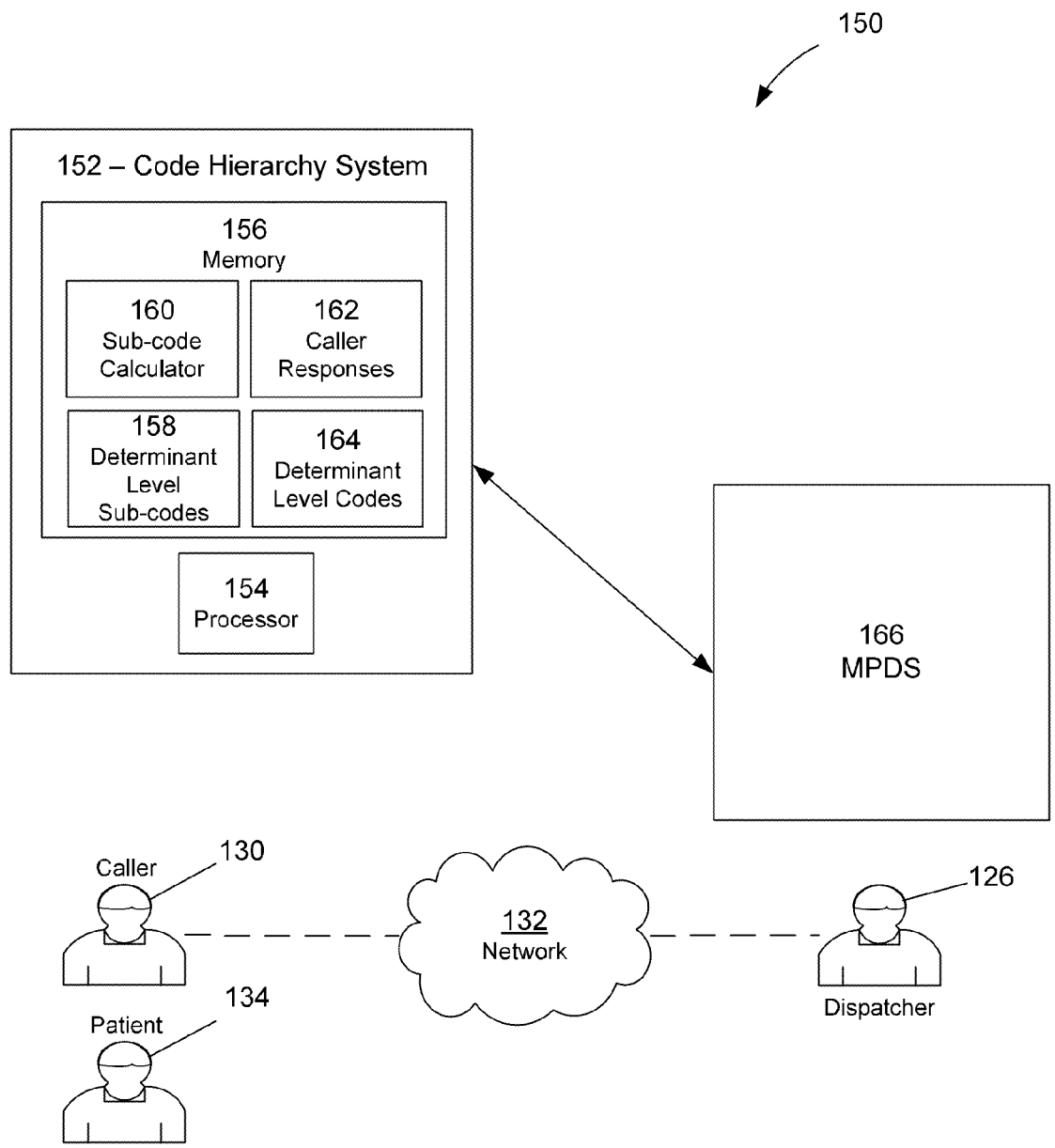
FIG. 1A depicts a block diagram of another embodiment of a system to identify code hierarchy bias in a medical priority dispatch system.

FIG. 1A depicts a block diagram of another embodiment of a computer system 150 to identify code hierarchy bias in an emergency medical dispatch system. The computer system 150 comprises a code hierarchy system 152, which may include a processor 154 and a memory 156. The memory may store determinant level sub-codes 158. The memory may further comprise a determinant level sub-code calculator 160 and storage for information received from an MPDS, such as caller responses 162 and determinant level codes 164. The code hierarchy system 152 interfaces with or is coupled to an MPDS 166. The MPDS may comprise a computer having a processor, input and output devices, and a memory having components such as a protocol module, pre-scripted inquiries, pre-scripted instructions, and a determinant value calculator module as described above with reference to FIG. 1. As can be appreciated, the embodiment of the computer system 150 of FIG. 2 may comprise a single computer. In another embodiment, the computer system 150 may comprise a first computer for the MPDS 166 and a second computer for the code hierarchy system 152 coupled together via a network.

An EMD 126 using the MPDS 166 can receive an emergency medical call from a caller 130, via a network 132, and can process the call according to a protocol of the MPDS 166. While the call is being processed, the MPDS 166 provides the EMD 126 with pre-scripted inquiries or questions and instructions for the caller 130, as previously described with reference to FIG. 1. The EMD 126 enters caller responses to the inquiries or questions about a patient 134 into the MPDS 166 and the MPDS 166 generates a determinant level code based on those caller responses.

The code hierarchy system 152 can receive the caller responses 162 and determinant level codes 164 from the MPDS 166. The caller responses 162 and determinant level codes 164 may be stored in the memory 156. The sub-code calculator module 160 can use the determinant level codes 164 and/or caller responses 162 to calculate a determinant level sub-code 158 to be output or stored. The determinant level codes and sub-codes can then be used to determine Code Hierarchy Bias.

Figure 2:
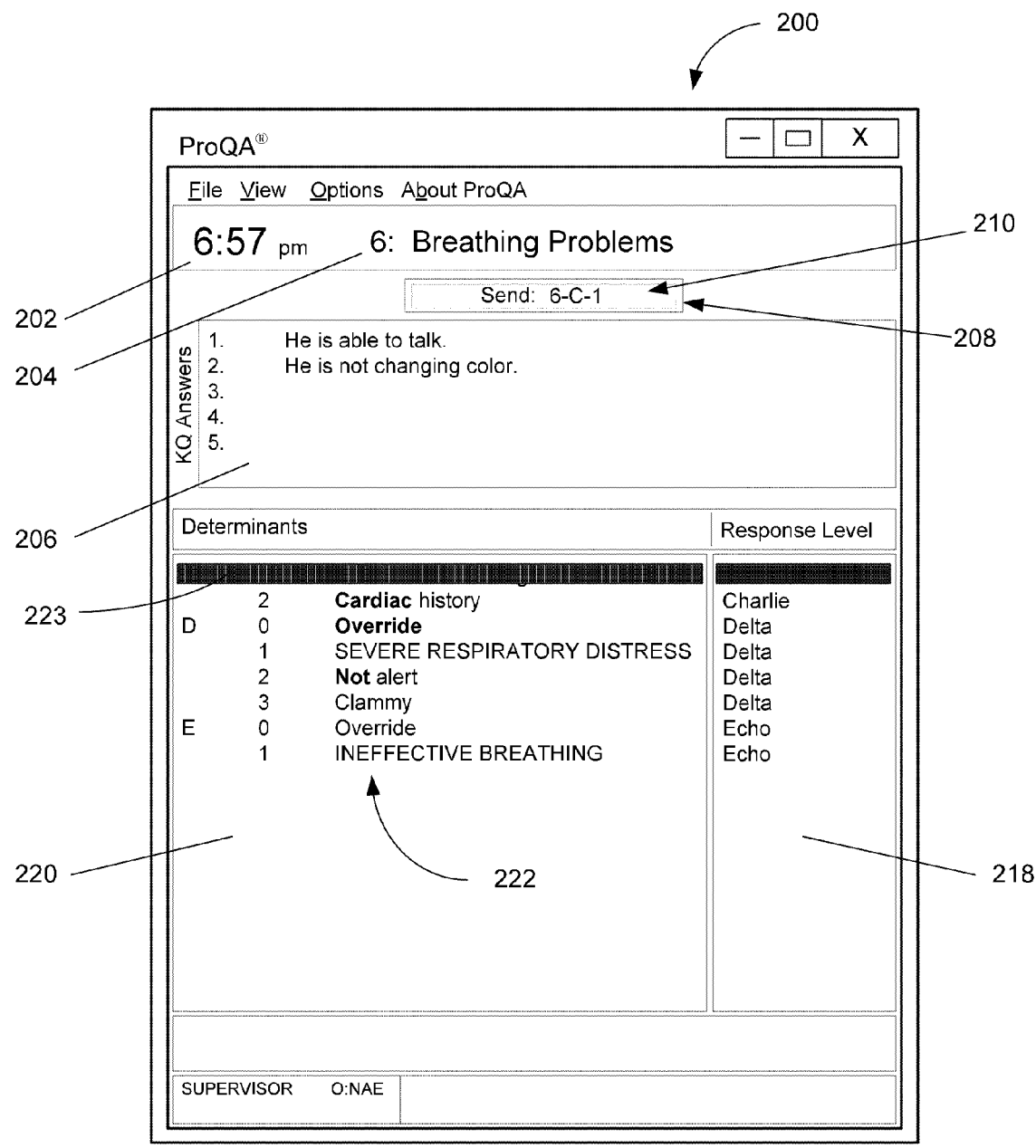
FIG. 2 depicts a display of one embodiment of a medical priority dispatch system.

FIG. 2 depicts a display of one embodiment of a display 200 of an MPDS traversing a protocol. The MPDS is at a point in the protocol where a determinant level code may be determined and selected. The display 200 is an output screen of a software program that implements a MPDS. The display 200 is shown when the MPDS is at a point in the protocol after multiple questions have been asked by the EMD and answered by the caller and a determinant level code is being determined by the EMD and/or the MPDS. The display 200 may comprise a clock 202 displaying the current time, a protocol indicator 204 signaling to an EMD the protocol the MPDS is currently following, an Answers pane 206, a determinant level code Send button 208, a display 210 on the Send button 208 to show the currently selected determinant level code, a Determinants pane 220, and a Response Level pane 118.

The protocol indicator 204, as shown in FIG. 2, indicates that the current protocol of the MPDS is Protocol 6, which guides an EMD in handling "Breathing Problems" related calls. Accordingly, the Determinants pane 220 displays a list of determinants 222 that can aid in categorizing and/or prioritizing the variations of breathing problems the patient may be experiencing. The determinants 222 comprise an emergency level descriptor and a determinant value. A brief description of what each determinant represents is also included in the Determinants pane 220.

The EMD directs inquiries or questions to the caller to identify the aspects of the patient's breathing problem. The caller's responses are entered into the MPDS to enable the MPDS to identify candidate determinants 222 to highlight in the Determinants pane 220. From the candidate determinants 222, the MPDS and/or the EMD can determine an appropriate determinant level code to send to the emergency response agency. The currently recommended (or EMD selected) determinant 222 may be highlighted by a selection cursor 223 in the Determinants pane 220. Other determinants 222 can match the symptoms, and thereby qualify as selection candidates that the EMD or the MPDS may select. These selection candidates can also be highlighted, for example in a different color, or otherwise indicated. In one embodiment, the EMD may select a candidate determinant 222 and thereby override a recommended MPDS selection.

The Answers pane 206 displays answers provided by the caller in response to questions generated by the MPDS protocol. The responses may be typed in by the EMD, or the field may be populated according to selections made by the EMD in another user interface. In one embodiment the Answers pane 206 may display all of the current caller's responses. In another embodiment, merely select caller responses may be displayed, such as those responses that trigger a higher determinant as a candidate. In still another embodiment, only the most recent caller responses are displayed. The caller responses may be numbered in the Answers pane 206. In FIG. 2, caller response 1 indicates the patient "is able to talk" and caller response 2 indicates the patient "is not changing color." Based on caller responses 1 and 2, the display 210 on the Send button 108 shows that the MPDS and/or the EMD has determined, thus far, that the proper determinant is "C-1 Abnormal breathing." A selection cursor 223 highlights the currently selected determinant in the Determinants pane 220.

In another embodiment, the lowest level determinant may be automatically selected as a default until a caller response triggers selecting a different determinant. The embodiment shown in FIG. 2 may be initially highlighting C-1 as a default determinant, although it may be the case that neither of the two responses received to this point would have triggered the C-1 determinant. In another embodiment, no determinant is selected until a caller response corresponds to a determinant.

The Response level for determinant C-1, as indicated in the Response Level pane 118, is Charlie. The Response level may be described as a higher level categorization of the situation, and may correspond to, and signal to the response agency, the level of emergency response needed. The response level can correspond to the emergency level descriptor of the corresponding determinant 222.

Figure 3A:
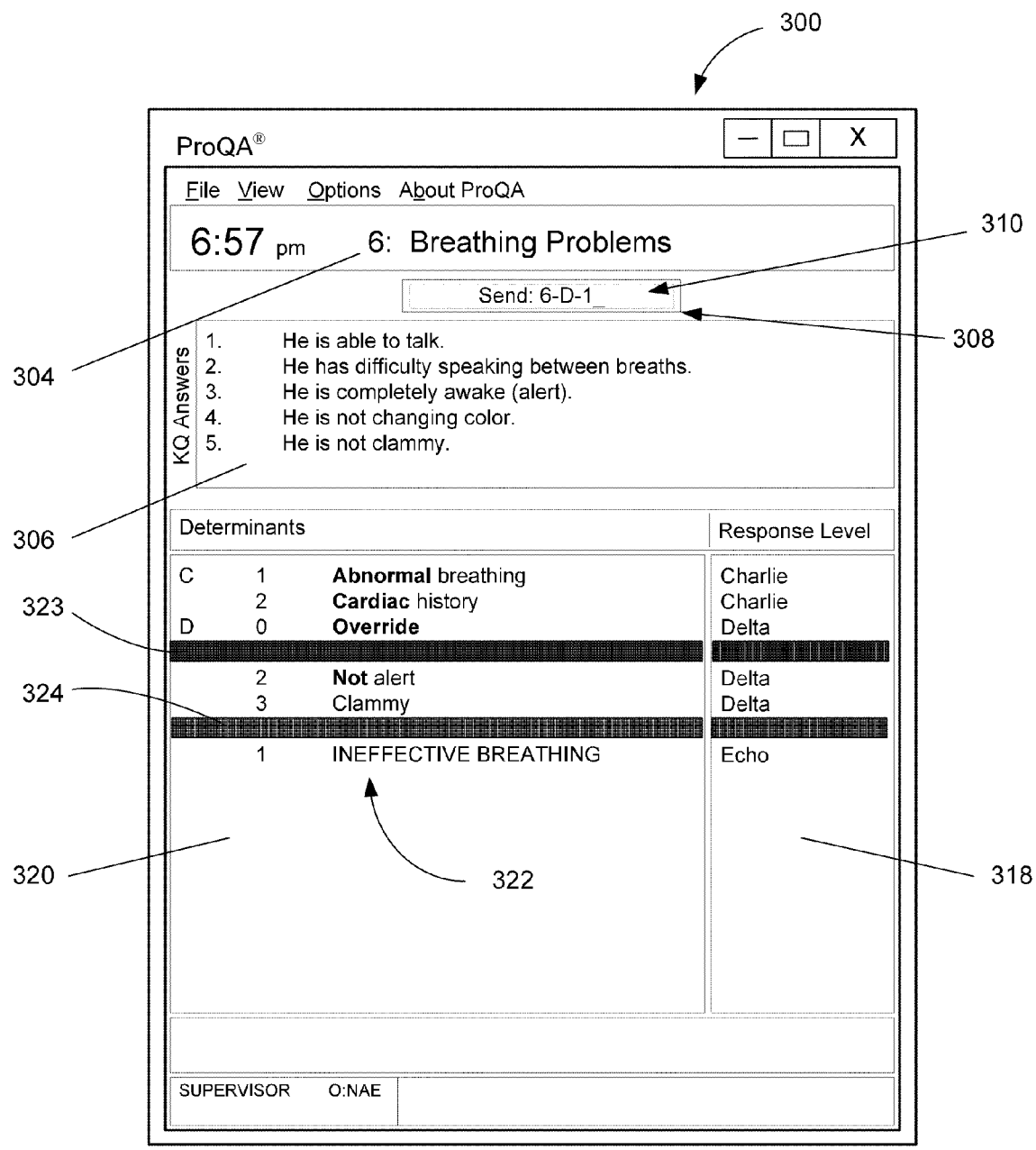
FIGS. 3A-3C depict a display of another embodiment of a medical priority dispatch system and illustrate stack Code Hierarchy Bias.
Figure 3B:
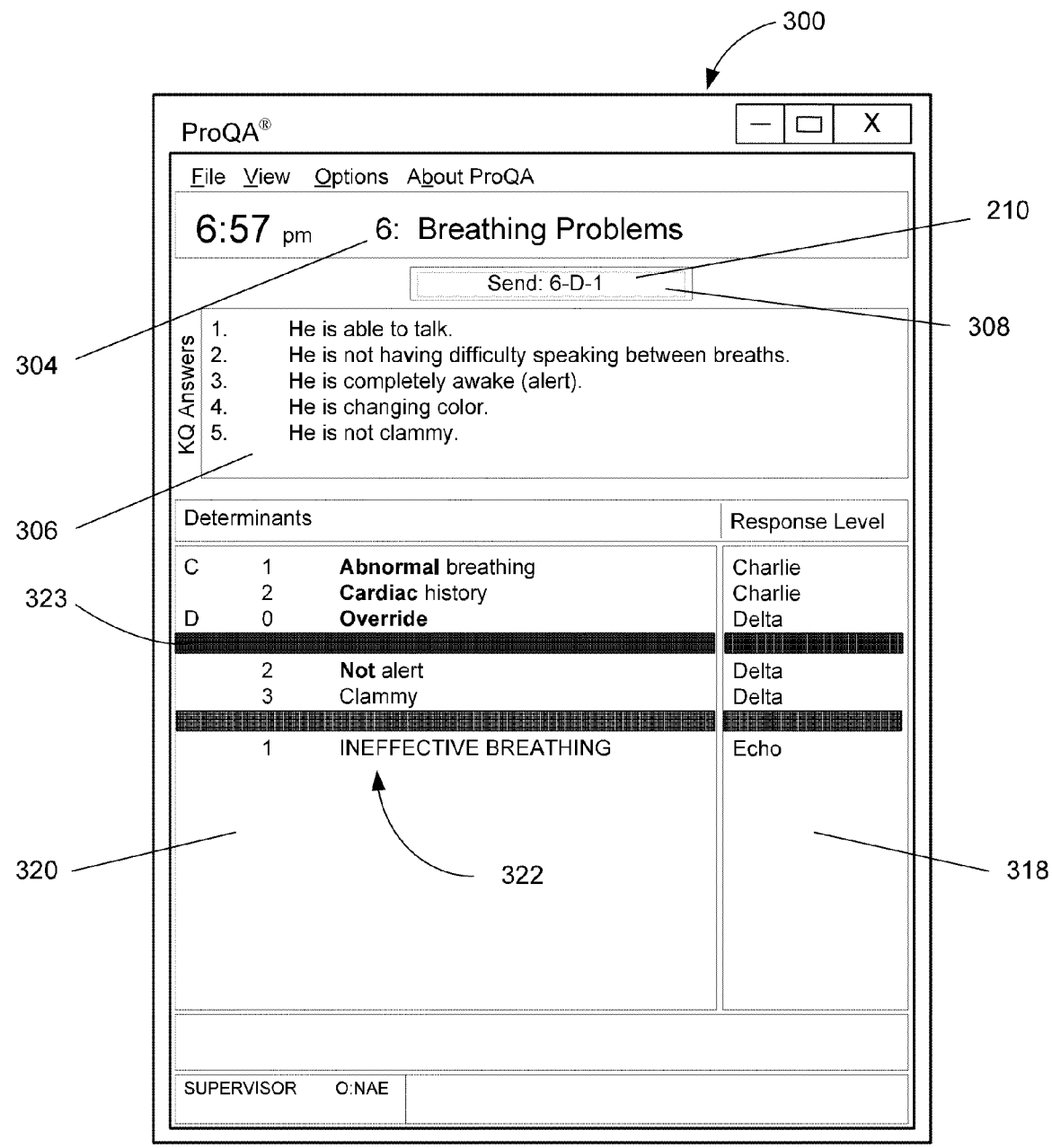
Figure 3C:
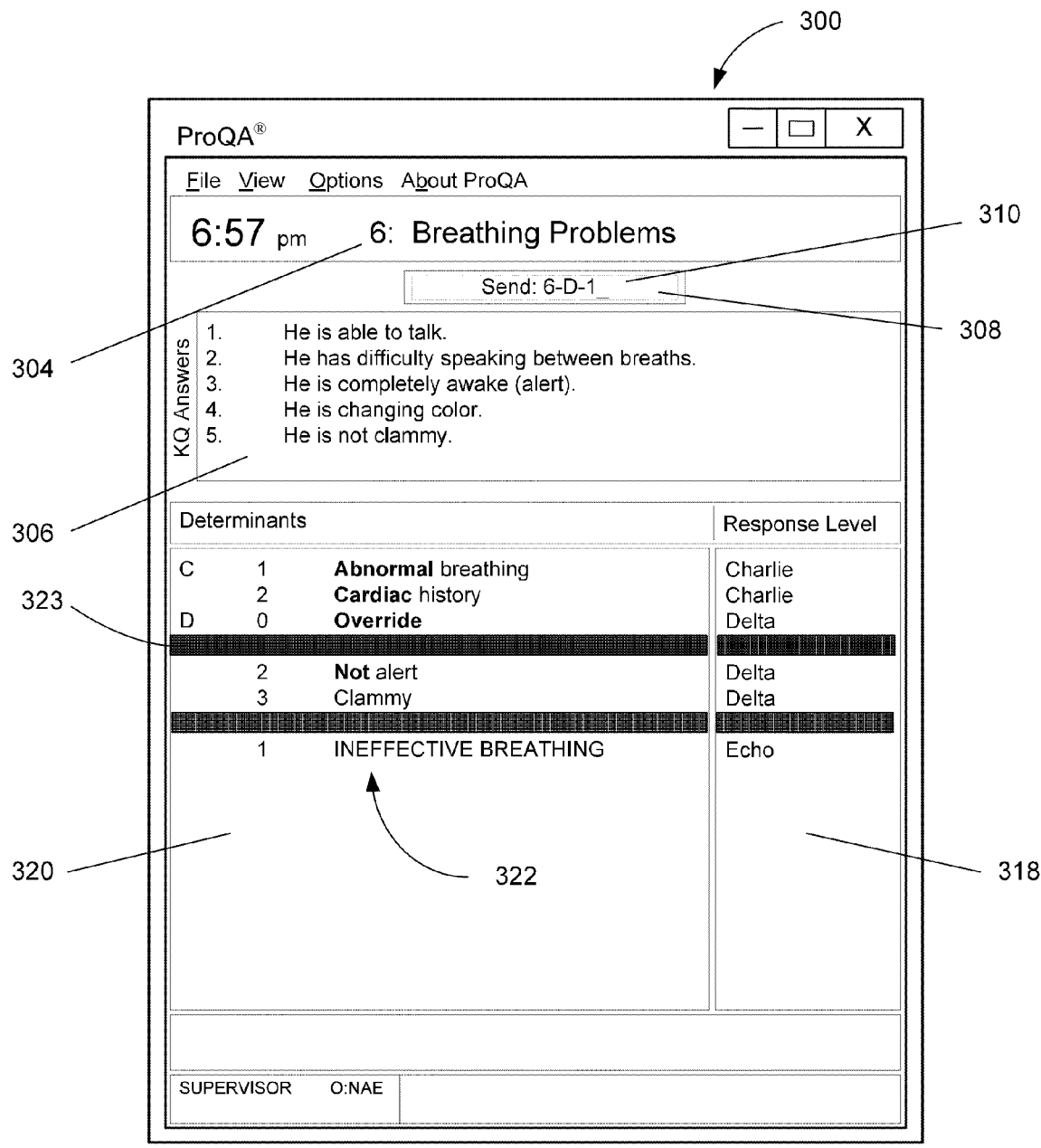
Figure 4A:
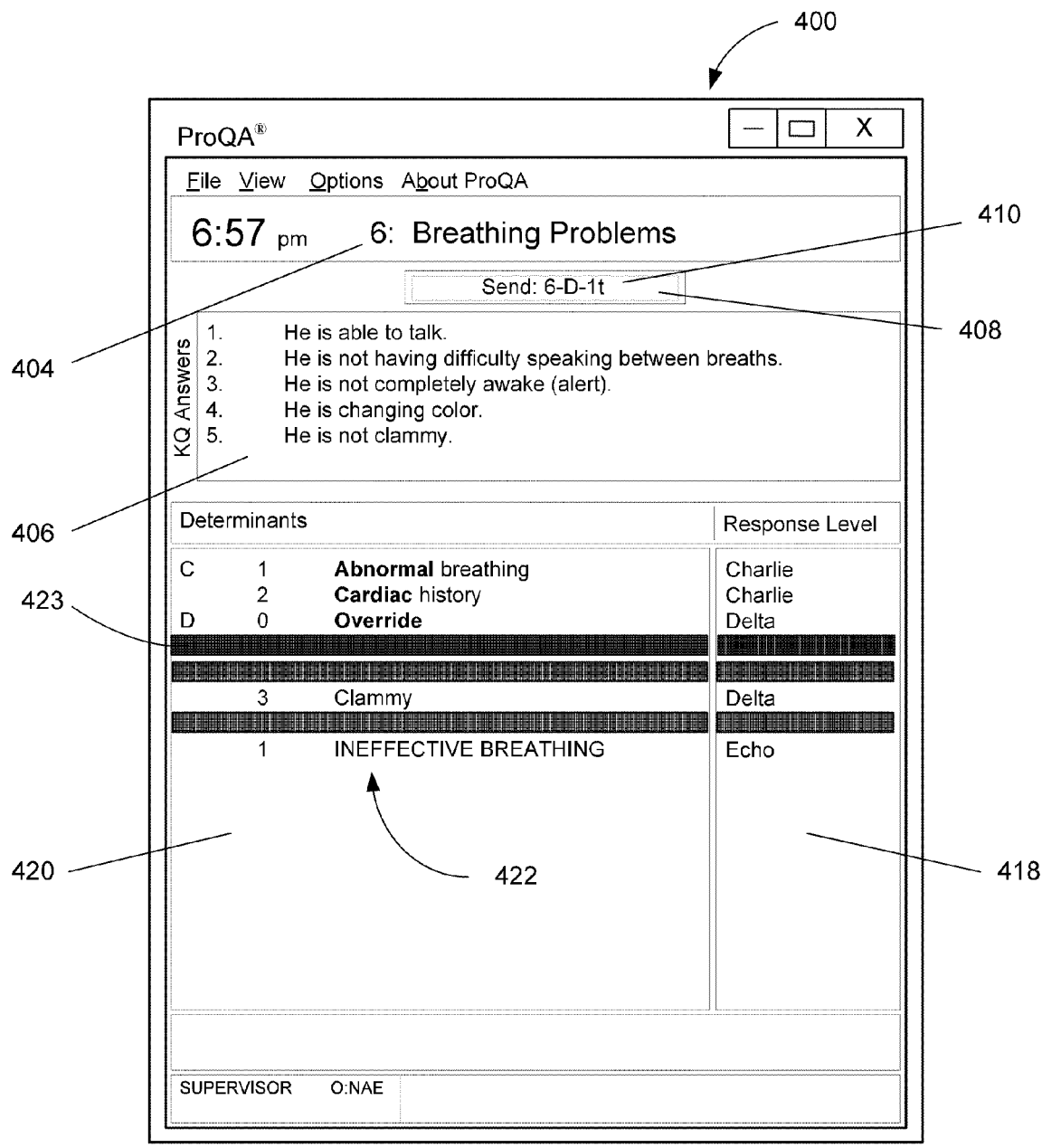
FIGS. 4A-4C depict a display of the embodiment of a medical priority dispatch system of FIGS. 3A-3C and illustrate dual Code Hierarchy Bias.
Figure 4B:
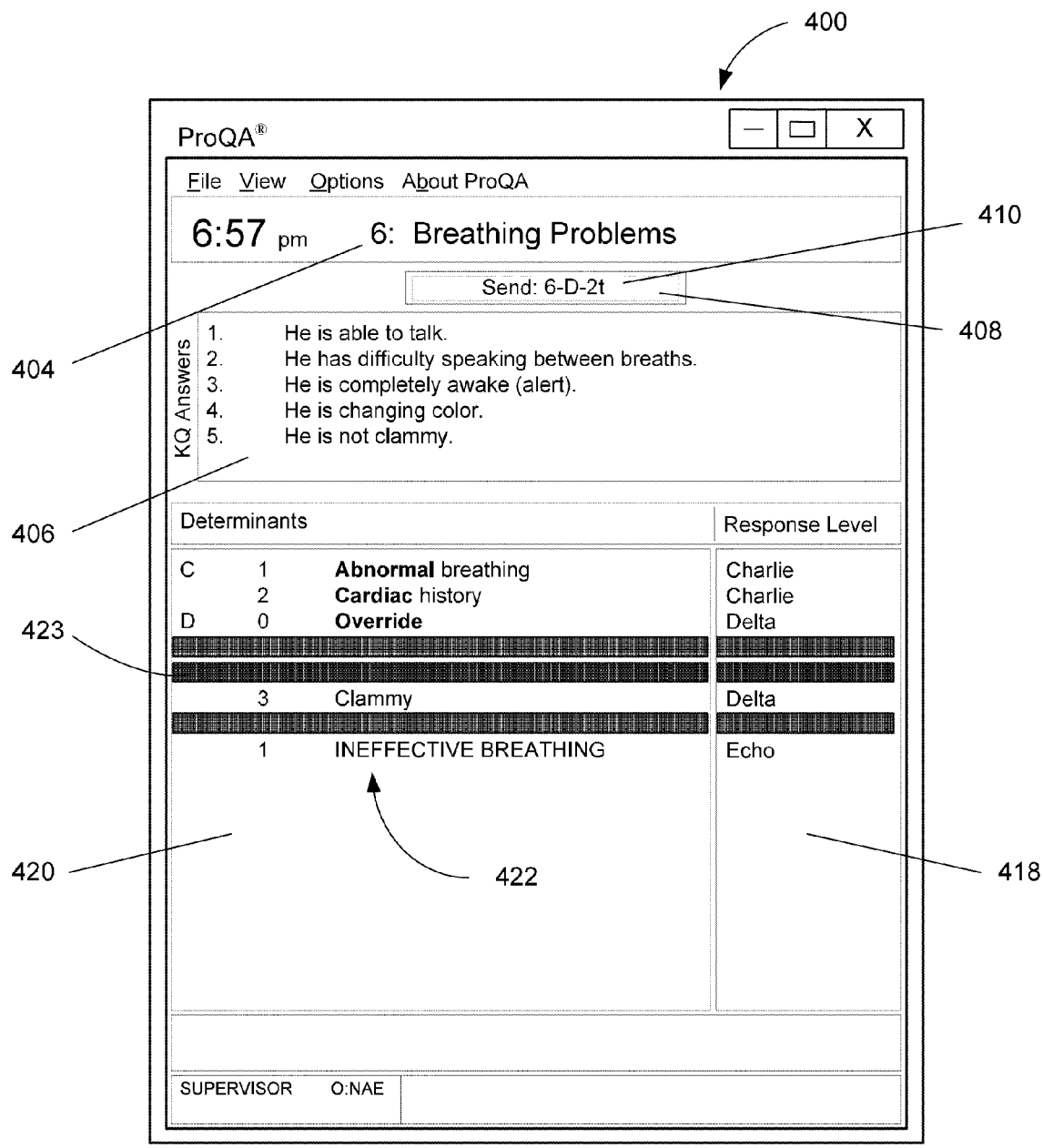
Figure 4C:
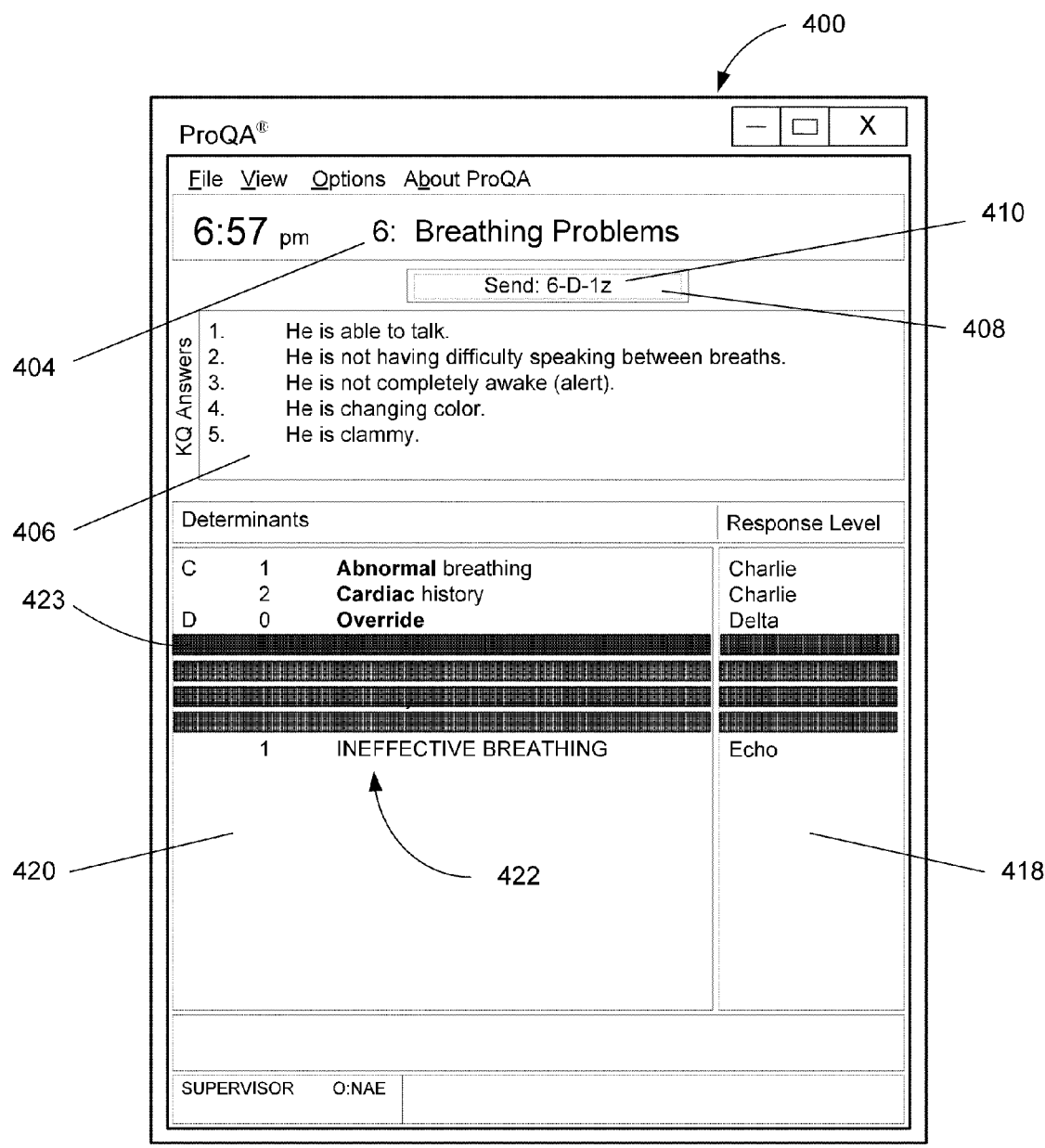

FIGS. 3A-4C aid in understanding Code Hierarchy Bias and the challenge addressed by the present invention. When multiple aspects of a situation are present and reported by a caller, the inherent nature of emergency medical dispatch introduces a potential for bias. The MPDS protocol generally may be designed and configured to identify the most critical situations by keying on the most critical aspects reported, and thereby filter and generalize emergency situations. Protocol 6, as depicted on the protocol indicator 304 in FIGS. 3A-3C and the protocol indicator 404 in FIGS. 4A-4C, is useful to demonstrate this filtering and generalizing, and the bias that may result.

FIGS. 3A-3C depict a display of another embodiment of a medical priority dispatch system. These figures illustrate a first type of bias, a stack bias, which is encountered when two or more aspects, including but not limited to signs, symptoms, or conditions, correspond to a defined determinant level code descriptor, as is the case with 6-D-1 Severe Respiratory Distress ("SRD"). Two aspects may trigger selection of the 6-D-1 SRD determinant level code: (1) the patient may be changing color, or (2) the patient may have difficulty speaking between breaths. If only the determinant level code is used and/or communicated, at times the actual nature of the problem being reported may be masked because it may be unclear which condition triggered the determinant. With two trigger aspects, there are three different medical situations covered by the 6-D-1 determinant level code descriptor, namely the patient may be suffering with either aspect, or with both aspects. More specifically, the patient could (i) be changing color, only, (ii) have difficulty speaking between breaths, only, or (iii) be changing color and have difficulty speaking between breaths. Thus, there is uncertainty as to which of the three is the exact situation when only the 6-D-1 code is communicated and/or recorded.

In FIG. 3A, the problem being reported is SRD due to 'difficulty speaking between breaths.' Based on responses 1-5 in the Answers pane 306, the display 310 on the Send button 308 in FIG. 3A shows that the MPDS and/or the EMD has determined the proper code to be sent is 6-D-1 for SRD. Specifically, response 2 in the Answers pane 306 indicates the EMD operating the MPDS is speaking to a caller that is reporting a patient manifesting difficulty speaking between breaths. The determinant D-1 is highlighted by the selection cursor 323 in the Determinants pane 320 to show it is currently selected. If only the determinant level code 6-D-1 is communicated to the emergency response agency, there is no way for the agency to determine that the response was triggered by "difficulty speaking between breaths" as opposed to "changing color." Further, if only 6-D-1 is recorded for subsequent research and analysis, there is no way to go back and determine which aspect(s) triggered the determinant. Even if the responses are also recorded, performing subsequent research and analysis on the data requires tediously reviewing each series of questions and caller responses and counting, or identifying the combination of, the aspects reported. Such tedious review is impractical and approaches impossible when the number of calls and cases to be analyzed is in the millions and when the total number of possible question and answer combinations currently exceeds 83 million.

In FIG. 3B, the problem being reported is also SRD, but this time the aspect being reported is that the patient is 'changing color' (rather than difficulty speaking between breaths). Based on responses 1-5 in the Answers pane 306, the display 310 on the Send button 308 in FIG. 3B shows that the MPDS and/or the EMD has determined the proper code to be sent is again 6-D-1 for SRD. Specifically, response 4 in the Answers pane 306 indicates the EMD operating the MPDS is speaking to a caller that is reporting a patient who is changing color, but who is not having difficulty speaking between breaths. The determinant D-1 is highlighted by the selection cursor 323 in the Determinants pane 320 to show it is currently selected. Again, if only the determinant level code 6-D-1 is communicated to the emergency response agency, or recorded for research purposes, there is no way to determine that the response was triggered by a patient who is changing color rather than who is having difficulty speaking between breaths.

In FIG. 3C, the problem being reported is again SRD, and this time both of the aspects of the determinant level code 6-D-1 are being reported. Based on the caller responses 1-5 in the Answers pane 306, the display 310 on the Send button 308 in FIG. 3C shows that the MPDS and/or the EMD has determined the proper determinant level code to be used is again 6-D-1 for SRD. Specifically, responses 2 and 4 in the Answers pane 306 indicate the EMD operating the MPDS is speaking to a caller that is reporting a patient manifesting both difficulty speaking between breaths and changing color. The determinant D-1 is highlighted by the selection cursor 323 in the Determinants pane 320 to show it is currently selected. Again, if only the determinant level code 6-D-1 is sent to the emergency response agency, or recorded for research purposes, there is no way to determine that the response was triggered by a patient who is manifesting both aspects included in the clinical definition of severe respiratory distress, rather than simply one or the other.

FIGS. 4A-4C depict a display of another embodiment of a medical priority dispatch system and illustrate another type of bias. This second type of Code Hierarchy Bias, a dual code bias, is encountered when the aspects, including but not limited to signs, symptoms, or conditions, of more than one determinant level code descriptor are present. For example, the signs and symptoms represented by determinant level codes "6-D-2 Not alert" or "6-D-3 Clammy" may also be present in a "6-D-1 SRD" coded patient. The signs and symptoms of these lower priority codes are hidden by the selection and sending of determinant level code "6-D-1."

In FIG. 4A, the problem being reported is again severe respiratory distress. However, the aspect of being "not alert" (which can be a factor for selecting the "D-2 Not Alert" determinant) is present in addition to the aspect of changing color, which triggers the "D-1 SRD" determinant. Based on responses 1-5 in the Answers pane 406, the MPDS and/or the EMD may have determined the proper determinant level code to be sent is again "6-D-1 SRD." Specifically, responses 3 and 4 in the Answers pane 406 indicate the EMD operating the MPDS is speaking to a caller that is reporting a patient who is not alert and who is changing color. The determinant D-1 is highlighted by the selection cursor 423 in the Determinants pane 420 to show it is currently selected. Again, if only the determinant level code 6-D-1 is sent to the emergency response agency, or recorded for research purposes, there is no way for the agency to determine that the patient is also manifesting the aspect of not being alert that triggers the second determinant D-2. Thus, dual code bias is introduced.

The MPDS of FIGS. 4A-4C, however, implements one embodiment of a method of the present disclosure to aid in identifying both stack and dual code bias. Specifically, in one embodiment of the present disclosure, an automated computer system and/or computer-implemented method operate in association with the MPDS to generate a determinant level sub-code based on a caller's responses. The determinant level sub-code represents a combination of reported aspects. For example, in FIG. 4A the display 410 on the Send button 408 indicates the determinant level code, and appends a determinant level sub-code, in this case "t". The sub-code "t" represents the combination of aspects 'changing color' AND 'not alert.' Including the sub-code "t" allows quick identification of all the aspects that were reported. The emergency response agency has more information available. Moreover, if the sub-code is recorded with the determinant level code, analysis can subsequently be performed to identify Code Hierarchy Bias and to assess the accuracy and usefulness of the determinant level code in communicating different emergency situations.

In FIG. 4B, the problem being reported manifests the same aspects as FIG. 4A above, namely changing color and not alert. In this case the MPDS and/or the EMD may have determined the proper determinant level code to be sent is "6-D-2 Not Alert." In another embodiment, the EMD may have overridden the MPDS determination. The determinant level D-1 SRD is highlighted as a candidate, but not currently selected. Rather the determinant D-2 Not Alert is highlighted by the selection cursor 423 in the Determinants pane 420 to show it is currently selected. If only the code 6-D-2 is sent to the emergency response agency, or recorded for research purposes, there is no way to determine that the patient is also manifesting the aspect of changing color. Nor is there any way to go back and investigate why the EMD or MPDS may have selected 6-D-2, or why the EMD may have overridden the system recommendation of sending 6-D-1, because there would be no record of the reported aspect of changing color.

The methods of the present disclosure capture more information, and thereby enable discovery of the nature of the bias. In addition to the determinant level code 6-D-2, the determinant level sub-code "t" is appended. As before, the sub-code "t" represents the combination of both aspects reported, 'changing color' AND 'not alert.' The sub-code "t" provides more information for identifying Code Hierarchy Bias and for improving the system.

FIG. 4C depicts a final example. In FIG. 4C, the patient is manifesting the same aspects as FIG. 4A above (changing color and not alert) and is also "clammy." Based on responses 1-5 in the Answers pane 406, the display 410 on the Send button 408 in FIG. 4C shows that the MPDS and/or the EMD has determined the proper determinant level code to be sent is again 6-D-1. Specifically, responses 3, 4, and 5 in the Answers pane 406 indicate the EMD operating the MPDS is speaking to a caller that is reporting a patient who is not alert, changing color, and clammy. The determinant D-1 SRD is highlighted by the selection cursor 423 in the Determinants pane 420 to show it is currently selected. Again, if only the determinant level code 6-D-1 is sent to the emergency response agency, or recorded for research purposes, there is no way for the agency to determine that the patient is also manifesting the aspects of not being alert and clammy. However, the display 410 on the Send button 408 indicates both the determinant level code and a determinant level sub-code "z". The sub-code "z" represents the combination of aspects 'changing color' AND 'not alert' AND 'clammy.' By generating a determinant level sub-code, the methods of the present disclosure capture and reveal more information, and enable discovery of the nature of any Code Hierarchy Bias that may be present.

One of ordinary skill in the art will readily recognize that the determinant level sub-code may be generated a variety of ways. In one embodiment, the method of the present invention may generate the determinant level sub-code concurrently, while the MPDS proceeds through a protocol. In another embodiment, the method may store the caller responses and subsequently search and analyze the stored caller responses after the determinant level code is determined. In still another embodiment, the method may search and analyze the stored caller responses after the determinant level code has been sent to the emergency response agency.

Figure 5:
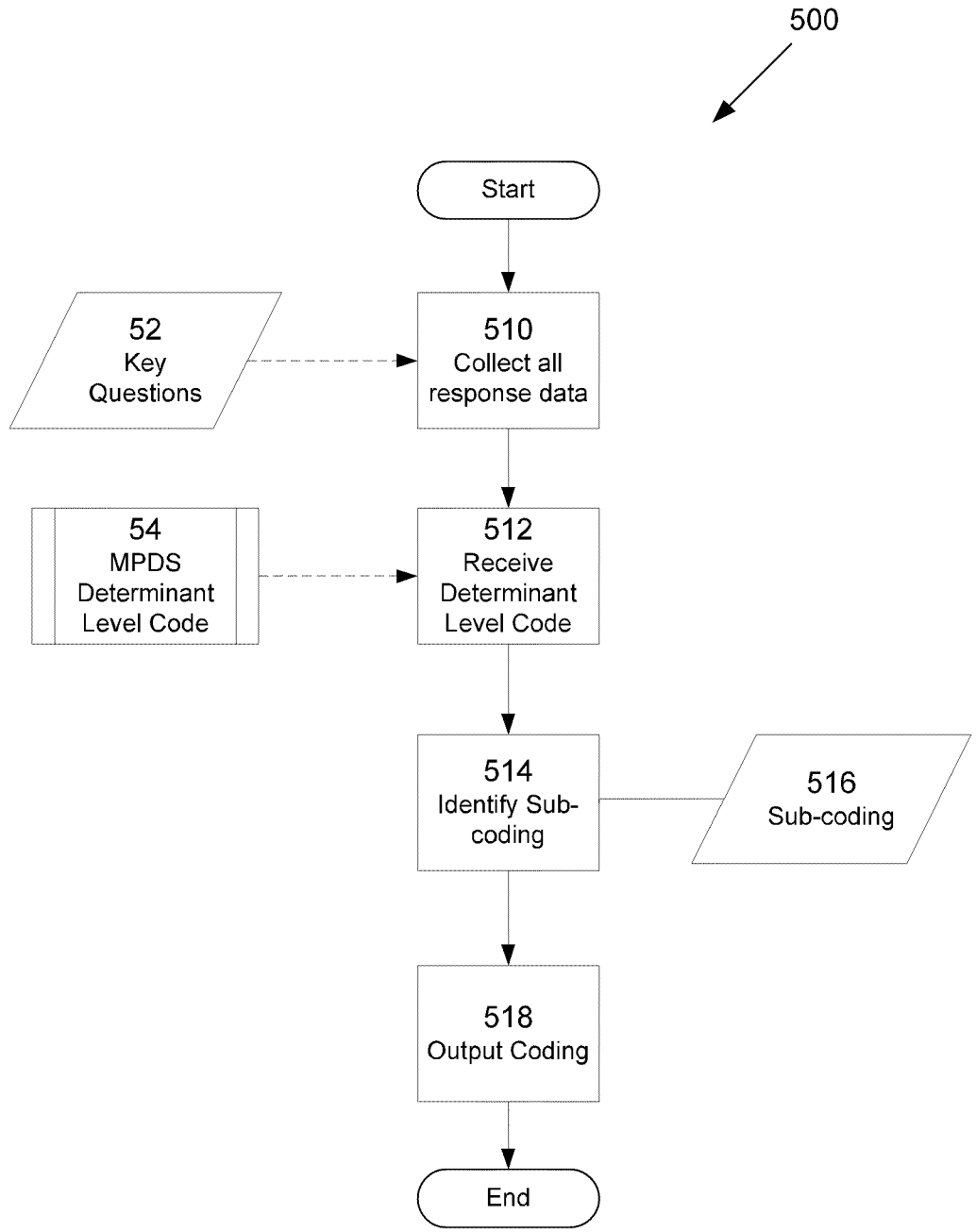
FIG. 5 depicts a flowchart of one embodiment of a method to determine Code Hierarchy Bias in a medical priority dispatch system.

FIG. 5 depicts a flow chart of one embodiment of a method 500 to determine Code Hierarchy Bias. The method 500 receives data from a MPDS, and generates a determinant level sub-code from the data received. The determinant level sub-code may be output. The method may start and may run concurrently while the MPDS traverses a protocol. Response data is collected 510 from caller responses to questions 52 generated by the MPDS protocol. The determinant level code 54 may also be received 512 from the MPDS protocol. The method 500 also may access 514 a file containing determinant level sub-codes 516. The determinant level sub-code can be calculated based on the caller response data received 510. The determinant level code and sub-code are combined and output 518 for transmission to the emergency response agency and/or storage. The method then ends. The output may be subsequently examined, analyzed, and/or compared with other output to similar cases to identify and reduce Code Hierarchy Bias and to improve the MPDS system or coding structure.

In another embodiment, the method 500 may run asynchronously with the MPDS, perhaps long after the MPDS has traversed the corresponding protocol. Response data is collected 510 from caller responses to questions 52 generated by the MPDS protocol. The responses may be collected 510 real-time from the MPDS, or may be retrieved from storage where they were previously recorded and fixed. Likewise, the determinant level code descriptor may be received real-time from the MPDS, or may be retrieved from storage where it was previously recorded and fixed. The output of the method 500 may be subsequently examined, analyzed, and/or compared with other output to similar cases to identify and reduce Code Hierarchy Bias and to improve the MPDS system or coding structure. For example, a determinant level code and determinant level sub-code pair may be compared to other determinant level code and determinant level sub-code pairs having the same determinant level sub-code. Because the determinant level sub-codes are identical, the same aspects were reported in each situation and the comparison can indicate the type of situations that are susceptible to Code Hierarchy Bias.

Figure 6:
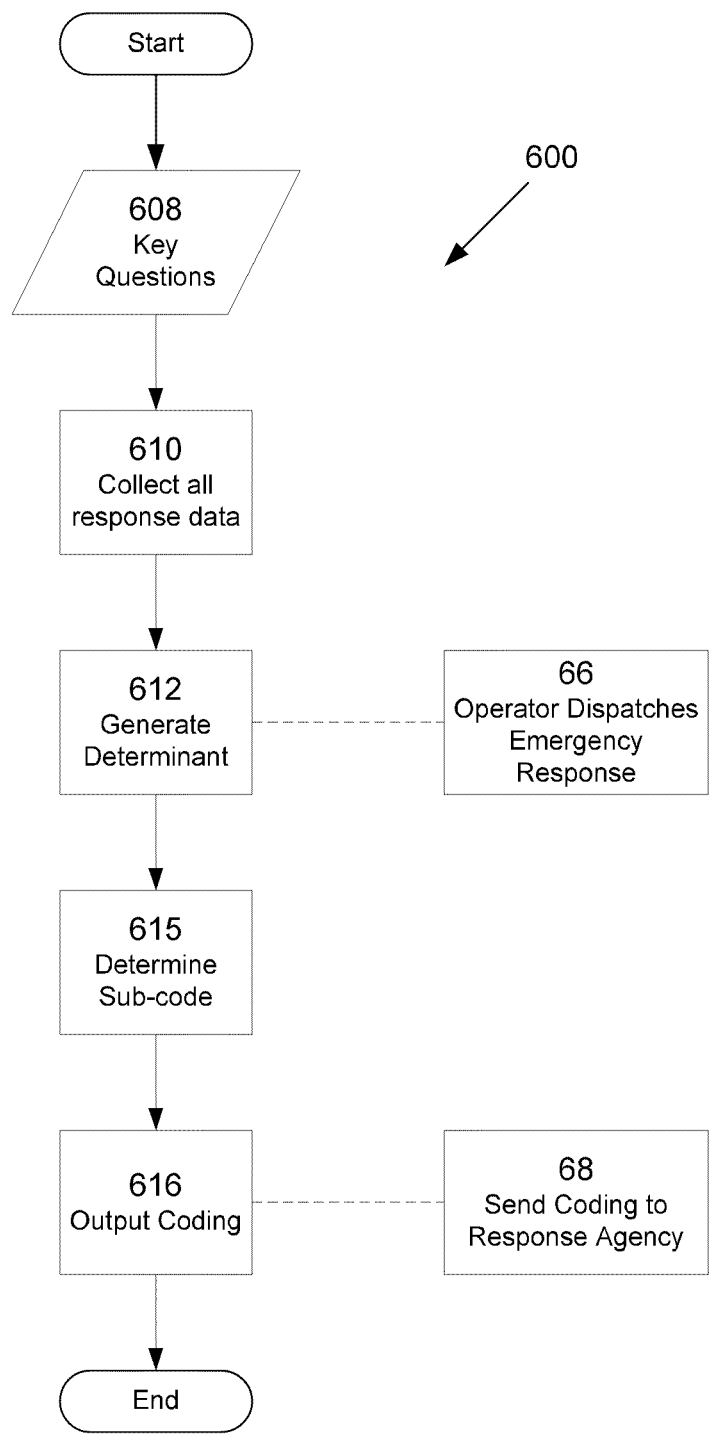
FIG. 6 depicts a flowchart of another embodiment of a method to determine Code Hierarchy Bias in a medical priority dispatch system.

FIG. 6 depicts a flow chart of another embodiment of a method 600 to determine Code Hierarchy Bias. This method may comprise steps generally performed by an MPDS. For example, the method 600 may generate 608 key questions to display to an EMD according to a protocol. The responses to the questions are collected 610 and then, similar to an MPDS, the data may be used to generate 612 a determinant level code that can be used to determine an appropriate emergency response to dispatch 66. The determinant level code can also be sent 68 to an emergency response agency. With response data and a determinant level code descriptor, an appropriate determinant level sub-code may be determined 615 and then output 616 with the determinant level code. The determinant level sub-code can also be sent 68 with the determinant level code to the response agency. In another embodiment, the method 600 can be incorporated into an MPDS protocol.

Figure 7:
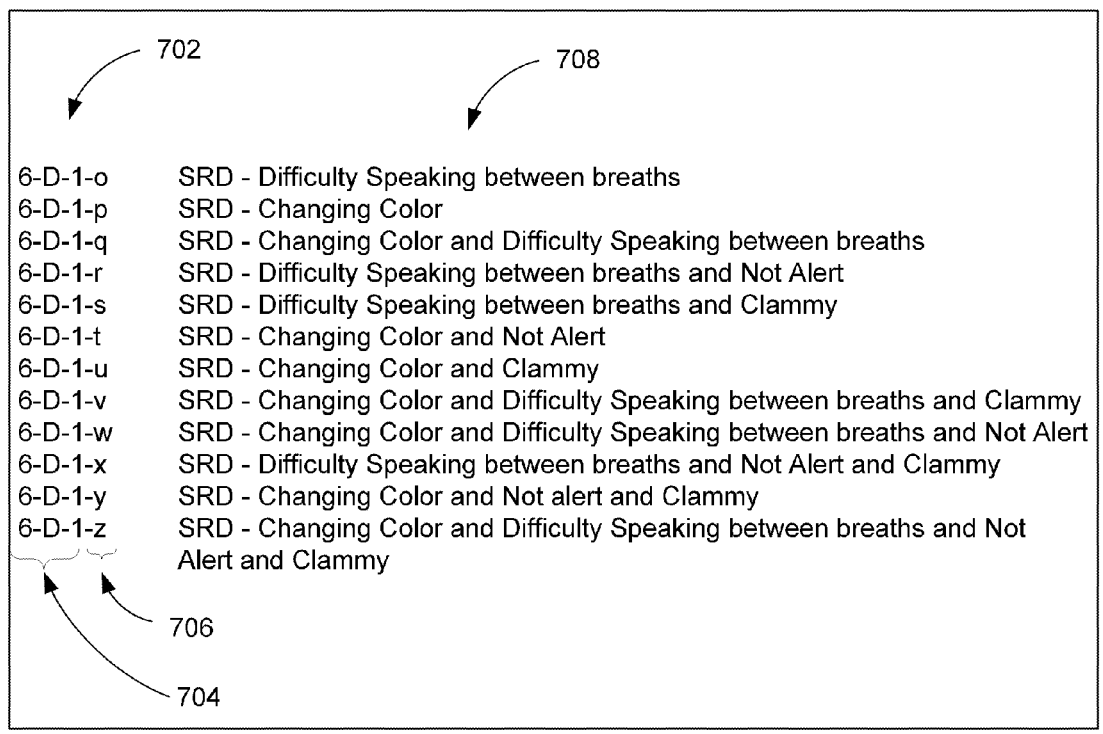
FIG. 7 depicts a list of determinant level code and determinant level sub-code combinations that may be output by one embodiment of a method to identify Code Hierarchy Bias in a medical priority dispatch system.

FIG. 7 depicts a list of potential combinations 702 of a determinant level code 704 and determinant level sub-codes 706 that may be output by one embodiment of a method to determine Code Hierarchy Bias in a MPDS. A description 708 is included for convenience in interpreting the combinations 702. As is apparent, the sub-codes 706 allow for creation of variations of the determinant level code 704. In this case, the determinant level code 704 is 6-D-1 and the potential combinations created with varying sub-codes 706 are shown. The various combinations 702 convey information that may otherwise not be generated or conveyed without the present invention. The list demonstrates that there are at least 12 possible clinical situations that may be included in what may have previously been a single code, namely determinant level code 6-D-1. That there are at least 12 possible combinations 702 illustrates the risk that an MPDS is cloaking signs, symptoms, and/or conditions and suggests the difficulty of revealing Code Hierarchy Bias without the embodiments of present disclosure.

Various modifications, changes, and variations apparent to those of skill in the art may be made in the arrangement, operation, and details of the methods and systems of the disclosure without departing from the spirit and scope of the disclosure. Thus, it is to be understood that the embodiments described above have been presented by way of example, and not limitation, and that the invention is defined by the appended claims.

What is claimed is:

1. A computer-implemented method to improve the clinical accuracy of determinant level codes generated by medical priority dispatch systems, the method comprising:

receiving at the computer system, from a medical priority dispatch system, one or more reported aspects collected from a caller who responds to questions asked by the dispatcher over a telephone, wherein the questions are provided to the dispatcher by the medical priority dispatch system and the reported aspects are relating to an emergency reported by the caller and are each one of the following: a sign, a symptom, and a condition;

receiving at a computer system, from a medical priority dispatch system, a determinant level code selected by a dispatcher utilizing the medical priority dispatch system, the determinant level code representing a subset of the reported aspects;

generating on the computer system a determinant level sub-code and pairing it with the determinant level code, wherein the determinant level sub-code is generated by the computer system based on the one or more reported aspects and represents a combination of all of the one or more caller reported aspects;

comparing on the computer system the determinant level code and determinant level sub-code pair to other determinant level code and determinant level sub-code pairs to identify whether a situation involving the reported aspects is susceptible to introducing code hierarchy bias; and outputting from the computer system information resulting from the comparison of determinant level code and determinant level sub-code pairs that enables improvements to the clinical accuracy of the determinant level codes generated by the medical priority dispatch system.

2. The computer-implemented method of claim 1, wherein the reported aspects include at least one of signs, symptoms, and conditions.

3. The computer-implemented method of claim 1, wherein comparing further comprises comparing determinant level code and determinant level sub-code pairs having the same determinant level sub-code.

4. The computer-implemented method of claim 1, further comprising storing the determinant level sub-code and the determinant level code in a non-transitory computer-readable storage medium.

5. The computer-implemented method of claim 1, wherein the determinant level sub-code is generated by selecting, from a list of sub-codes, a sub-code that represents the combination of all of the one or more caller reported aspects, wherein the list of sub-codes comprises possible combinations of aspects that may be reported by the caller in responses to the protocol questions.

6. The computer-implemented method of claim 1, further comprising storing the determinant level code and the corresponding reported aspects collected from the caller in a non-transitory computer-readable storage medium, wherein the computer system retrieves the determinant level code and the corresponding reported aspects and generates the determinant level sub-code.

7. A computer-implemented method for enabling evaluation and research of code hierarchy bias in medical priority dispatch systems, the method comprising:

receiving, at a medical priority dispatch computer system, caller responses to questions provided by the medical priority dispatch system, the responses reporting one or more signs, symptoms, or conditions relating to an emergency reported by the caller;

generating a determinant level code based on the caller responses and relaying the determinant level code to emergency responders, the determinant level code representing a subset of the caller-reported signs, symptoms, or conditions relating to the emergency;

generating, at the medical priority dispatch computer system, a determinant level sub-code based on the caller responses by selecting a sub-code representing a combination of all of the caller-reported signs, symptoms, and conditions, the sub-code selected from a list of sub-codes representing potential combinations of signs, symptoms, and conditions that can be reported in the caller responses; and the medical priority dispatch system storing the determinant level sub-code in combination with the determinant level code in a non-transitory computer-readable storage medium.

13

8. The computer-implemented method of claim 7, further comprising storing the caller responses in a non-transitory computer-readable storage medium for subsequent examination to generate the determinant level sub-code.

9. The computer-implemented method of claim 7, further comprising the medical priority dispatch computer system comparing determinant level code and determinant level sub-code pairs to identify whether a combination of reported aspects in a given situation is susceptible to code hierarchy bias.

10. The computer-implemented method of claim 9, wherein the medical priority dispatch computer system comparing further comprises comparing determinant level code and determinant level sub-code pairs having the same determinant level sub-code.

11. The computer-implemented method of claim 7, further comprising performing statistical analysis on a plurality of stored determinant level code and sub-code combinations to determine situations that are susceptible to code hierarchy bias.

12. The computer-implemented method of claim 7, further comprising performing statistical analysis on a plurality of stored determinant level code and sub-code combinations to determine a clinical make-up of the determinant level code as it relates to specific situations and diagnoses and to ensure the determinant level codes are medically accurate.

13. A computer-implemented method for emergency medical dispatch response, the method comprising:
receiving at a computer system caller responses to questions asked by a dispatcher, the responses reporting aspects, including signs, symptoms, or conditions, relating to an emergency, wherein the responses are input into the computer system by the dispatcher, and wherein the questions are provided to the dispatcher according to a pre-scripted protocol by a medical priority dispatch system running on the computer system;
the computer system and dispatcher generating a determinant level code indicative of the criticality of the call based on the caller responses, the determinant level code representing a subset of the caller-reported aspects relating to the emergency;
the computer system generating a determinant level sub-code based on a combination of signs, symptoms, and conditions reported in the caller responses to the protocol questions, the sub code representing the combination of all of the reported signs, symptoms, and conditions;
the computer system storing the determinant level code and the determinant level sub-code pair; and
the computer system communicating to an emergency response agency the determinant level code and determinant level sub-code.

14. The computer-implemented method of claim 13, further comprising the computer system storing the caller responses on a non-transitory computer-readable storage medium for subsequent examination to generate the determinant level sub-code, wherein the computer system generates the determinant level sub-code by electronically searching and analyzing the caller responses to generate the determinant level sub-code.

15. The computer-implemented method of claim 13, further comprising the computer system performing statistical analysis on stored determinant level code and sub-code data to determine situations that are susceptible to code hierarchy bias.

16. The computer-implemented method of claim 13, further comprising the computer system performing statistical analysis on stored determinant level code and sub-code descriptor data to determine a clinical make-up of each determinant level code as it relates to specific situations and diagnoses and to ensure the determinant level codes are medically accurate.

17. A computer system for identifying code hierarchy bias in a medical priority dispatch system, the computer system comprising:
a medical priority dispatch system to generate a determinant level code indicative of the criticality of the call based on caller responses to questions asked by a dispatcher, wherein the questions are provided to the dispatcher according to a pre-scripted protocol by the medical priority dispatch system, and wherein the responses report a plurality of aspects and the determinant level code represents a subset of the plurality of aspects, each aspect of the plurality of aspects comprising one of the following: a sign, a symptom, a condition;
a code hierarchy system in communication with the medical priority dispatch system, the code hierarchy system configured to receive the determinant level code generated on the medical priority dispatch system, to generate a determinant level sub-code based on a combination of aspects reported in the caller responses to the questions asked by the dispatcher, to store the determinant level code and the determinant level sub-code pair; and communicate to an emergency response agency the determinant level code and determinant level sub-code,
wherein the determinant level sub-code represents the combination of all reported aspects,
wherein the computer system compares the determinant level code and determinant level sub-code pair to other determinant level code and determinant level sub-code pairs to identify whether a combination of reported aspects of a situation is susceptible to code hierarchy bias and outputs information resulting from the comparison of determinant level code and determinant level sub-code pairs that can be used to improve the clinical accuracy of the determinant level codes generated by the medical priority dispatch system.

18. The computer system of claim 17, wherein the computer system compares the determinant level code and determinant level sub-code pair to other pairs by performing statistical analysis to identify situations susceptible to code hierarchy bias.

19. The computer system of claim 17, wherein the medical priority dispatch system is on a first computer and the code hierarchy system is on a second computer, and wherein the computer system further comprises a network to enable communication between the first computer and the second computer.

20. A computer system for identifying code hierarchy bias in medical priority dispatch systems, the computer system comprising:
a processor;
an output device;
an input device;
a memory having stored thereon:
pre-scripted inquiries to be directed to an emergency caller by a dispatcher utilizing the computer system;
pre-scripted instructions to be provided to an emergency caller by the dispatcher;
a protocol module configured to present, on the monitor, the pre-scripted inquiries and instructions to the dispatcher; and
a calculator module configured to determine a determinant level code and a determinant level sub-code based on caller responses to the pre-scripted inquiries, wherein the caller responses report aspects, including signs, symptoms, and conditions, wherein the determinant level code represents a subset of the reported signs, symptoms, and conditions, and wherein the determinant level sub-code represents an entire combination of all the signs, symptoms, and conditions that are reported in the caller responses.

21. A computer system of claim 20, wherein the memory further comprises caller responses received from one or more callers responding to the pre-scripted inquiries, wherein the caller responses are stored on the memory to be subsequently searched and analyzed.

22. A computer system of claim 20, wherein the memory further comprises stored determinant level code and stored determinant level sub-codes.

* * * * *